United States Patent [19]
Mikami et al.

[11] Patent Number: 6,033,656
[45] Date of Patent: Mar. 7, 2000

[54] METHOD OF PREVENTING OR ALLEVIATING MAMMALIAN OBESITY

[75] Inventors: Toshiyuki Mikami, Ibaraki, Japan; Bruce Spiegelman, Waban; Harold Wright, Watertown, both of Mass.

[73] Assignees: Sumitomo Chemical Company, Limited, Osaka, Japan; Dana-Farber Cancer Institute, Inc., Boston, Mass.

[21] Appl. No.: 09/304,641

[22] Filed: May 4, 1999

[51] Int. Cl.$^7$ .............................. A61K 31/74; C08K 3/20; C08K 3/00; C08K 63/00

[52] U.S. Cl. ........................ 424/78.3; 424/78.3; 424/79; 424/78.17; 523/402; 523/400; 523/427

[58] Field of Search .................... 525/4.1; 260/112 B; 527/204; 424/79, 78.3; 8/115.61; 252/182.31; 523/402, 400

[56] References Cited

U.S. PATENT DOCUMENTS

| | | | |
|---|---|---|---|
| 3,935,173 | 1/1976 | Ogasawara et al. | 260/78.5 |
| 4,323,486 | 4/1982 | Suzuki et al. | 525/54.1 |
| 4,777,042 | 10/1988 | Toda et al. | 424/78.1 |

*Primary Examiner*—Keith D. Macmillan
*Assistant Examiner*—Vickie Kim
*Attorney, Agent, or Firm*—Birch, Stewart, Kolasch & Birch, LLP

[57] ABSTRACT

The present invention provides methods of suppressing the activation of Peroxisome Proliferator-Activated Receptor gamma in a mammalian body by administering an effective amount of bisphenol A diglycidyl ether to a mammal, methods of suppressing the accumulation of fat in the mammalian fat cell or adipose tissue by administering an effective amount of bisphenol A diglycidyl ether to a mammal, methods of preventing or alleviating mammalian obesity by administering an effective amount of bisphenol A diglycidyl ether to a mammal, bisphenol A diglycidyl ether for use as an active pharmaceutical substance or composition for the treatment of obesity, and uses of bisphenol A diglycidyl either for the preparation of a pharmaceutical composition for the treatment of obesity.

18 Claims, No Drawings

METHOD OF PREVENTING OR ALLEVIATING MAMMALIAN OBESITY

BACKGROUND OF THE INVENTION

1. Field of the Invention

The present invention relates to a method of preventing or alleviating mammalian obesity.

2. Description of the Related Art

Fat cells have the ability to store fat in their cells and are typically present in the adipose tisses of the subcutaneous abdominal region, the femoral region, the gluteal region, the pectoral region and the like, and the adipose tissues which are in the abdominal cavity and in the vicinity of the mesenterium, kidney, epididymis, and the like, which are in the body of a mammal, such as a human. For example, promoting the storage of fat in fat cells generally results in an obese mammal, which is generally accompanied by an increase in body fat content and an increase in the mass of adipose tissue which is typically in the abdominal cavity of the mammal. It is knovwn that such obesity thereby induces disorders such as the impairment in glucose tolerance [Journal of Clinical Investigation, vol.72, pp. 1150 (1983)], diabetes [National Diabetes Data Group: Diabetes in America. Bethesda, Md., U.S. Dept. of Health and Human Services, (1985), Diabetes Care, vol.19, pp.613 (1996), Diabetes & Metabolisme, vol.20, pp.375 (1994), Obesity: Advances in Understanding and Treatment, Published by IBC Biomedical Library, Chapter 3.1, (1996)], hyperglycemia, hyperlipemia, hypertension [Journal of Clinical Investigation, vol.72, pp. 1150 (1983)], coronary arterial diseases [Diabetes & Metabolisme, vol.20, pp.375 (1994)], obstructive arterial sclerosis and the like [WHO Expert Committee on Diabetes Mellitus. Second report, WHO Tech Rep 646 Geneva: World Health Organization (1980)].

The fat cells are generally produced by differentiating progenitor fat cells. To differentiate progenitor fat cells into fat cells, it is essential to activate a function of a protein called Peroxisome Proliferator-Activated Receptor gamma (hereinafter refereed to as "PPAR γ")[Peter Tontonoz, et al., Cell, vol.79, 1147–1156, 1994]. For example, the accumulation of fat in a fat cell can occur from having a thiazolidinedione derivative bind to PPAR γ in the progenitor fat cell so that PPAR γ can be activated, which induces the differentiation of the progenitor fat cell to a fat cell, and which then further expresses genes associated with fat accumulation [Jurgen of M. Lehman, et al., Journal of Biological Chemistry, vol. 270, No. 22, 12953–12956, 1995]. PPAR γ is a nuclear receptor type transcription regulating factor [Issenman and Green, Nature 347-645-650 (1990)].

Accordingly, there is a demand for the development of drugs which are effieffective in suppressing die increase in body fat content and the increase in the mass of adipose tissues, by suppressing the differentiation of the progenitor fat cell to the fat cell and further tile accumulation of fat in the fat cell and, as a result, preventing or alleviating obesity. Such drugs are expected to be effective for preventing or treating various diseases derived from obesity.

SUMMARY OF THE INVENTION

One objective of the present invention is to provide a method of suppressing the activity of mnammalian PPAR γ.

Another objective of the present invention is to provide a method of suppressing the accumulation of fat in a mammalian fat cell.

A further objective of the present invention is to provide a method of preventing or alleviating mammalian obesity.

These and other objects and advantages will be apparent from the following description.

Under the above circumstances, the Inventors have studied intensively, and as a result, have discovered that bisphenol A diglycidyl ether (hereinafter referred to as "BADGE"), which is given in the formula:

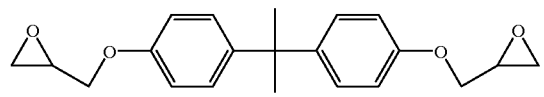

has an action of suppressing the activation of PPAR γ and an action of suppressing the accumulation of fat in a fat cell due to suppressing the activation of PPAR γ, and have arrived at the present invention.

In other words, the present invention provides methods of suppressing the activation of PPAR γ in a mammalian body by administering an effective amount of BADGE to a mammal, methods of suppressing the accumulation of fat in the mammalian fat cell by administering an effective amount of BADGE to a mammal, methods of preventing or alleviating mammalian obesity by administering an effective amount of BADGE to a mammal, BADGE for use as an active pharmaceutical substance or composition for the treatment of obesity, and uses of BADGE for the preparation of a pharmaceutical composition for the treatment of obesity.

DETAILED DESCRIPTION OF INVENTION

As used herein, throughout this specification and the claims which follow, unless the text requires otherwise, the word "comprise", "contain", "have", and the like, and variations thereof such as "comprises", "contains", "comprising", "containing", "having", and the like, will be understood to imply the inclusion of an integer or step or group of integers or steps which is stated herein, but not the exclusion of any other integer or step or group of integers or steps.

BADGE can be prepared, for example, by according to the method described in JP-B-52-46931 and purified by conventional methods such as liquid chromatography, recrystallization, or the like.

BADGE has the action of inhibiting the activation of PPAR γ, and thereby can suppress the accumulation of fat in a fat cell, and can prevent or alleviate obesity derived from the increase in body fat content or the increase in the mass of adipose tissues. More particularly, BADGE can be utilized as agents which suppress the activation of PPAR γ in the body of a mammal such as humans (hereinafter referred to as "PPAR γ activation suppressor"), agents which suppress the accumulation of fat in a fat cell which is in the body of a mammal such as humans (hereinafter referred to as "fat accumulation suppressor"), or agents which prevent or alleviate obesity of a mammal such as humans (hereinafter referred to as "obesity preventing or alleviating agent").

In this regard, due to such obesity prevention or alleviation, BADGE may be utilized for preventing or treating the various mammalian disorders which are typically accompanied with obesity such as the impairment in glucose tolerance, diabetes, hyperglycemia, hyperlipemia, hypertension, coronary arterial diseases, obstructive arterial sclerosis, and the like.

When BADGE is utilized as a PPAR γ activation suppressor, a fat accumulation suppressor, or an obesity preventing or alleviating agent, the effect of BADGE is achieved by orally or parenterally administering an effective amount of BADGE to a mammal such as humans. In this regard, examples of such an administering include methods of orally administering BADGE in a conventional form such as a tablet, capsule, syrup, suspension or the like, and methods of parenterally adrministering BADGE, such as injecting BADGE in a convention form such as a solution, emulsion, suspension or the like. In addition, another example of a method of parenterally administrating BADGE includes a method for rectally administering BADGE in the form of a suppository.

The above forms of dosage can usually be prepared by incorporating BADGE into a conventional carrier, excipient, binder, stabilizer, diluent or the like, or a combination thereof. In addition, when BADGE is used in the injection forms of the instant invention, an acceptable buffer, solubilizer, isotonicity or the like may be added thereto. The amount or frequency of a dosage of BADGE depends upon the symptom(s), age and weight of the mammal, as well as the dosage form of BADGE, but the dosage of BADGE is typically given to adults (i.e., adult humans) in an amount of from about 1 to 2000 mg per day, preferably about 5 to 1000 mg per day when orally administering BADGE, and about 0.1 to 500 mg per day when injecting BADGE, wherein said amounts may be given in one administration or divided into a multiplicity of administrations.

EXAMPLES

Example 1

An expression plasmid for the ligand binding region of PPAR γ, which has a polyhistidine fused to the N-terminus of said ligand binding region, was prepared in accordance to the method in Steven A. Kliewer, et al (Cell 83, 813–819, 1995) and was introduced into *Escherichia coli* BL21(DE3) plysS. The resulting recombinant *Escherichia coli* was inoculated in 30 ml of LB medium (1 w/v % of tryptone, 0.5 w/v % of yeast extract, and 0.5 w/v % of NaCl) containing 50 μg/ml ampicillin, and that was cultured and shook overnight at 37° C. Then, after 15 ml of the achieved culture was inoculated in 500 ml of LB medium (1 w/v % tryptone, 0.5 w/v % yeast extract, and 0.5 w/v % NaCl) containing 50 μg/ml ampicillin and was cultured and shook at 37° C. for 2 hours, IPTG (isopropyl-β-D-thiogalactopyranoside) was added to the culture so that the final concentration of IPTG was 0.5 mM therein, and that was fiarter cultured at 20° C. for 4 hours. After the *Escherichia coli* cells were recovered by centrifuiging the achieved culture, said cells were punctured by using ultrasound, and were then centrifuged so that the supernatant of the punctured cells can be collected. Ten milliliters (10 ml) of the achieved supernatant was loaded onto a column containing 1 ml of a nickel bound affinity carrier Ni-NTA, commercially available from QIAGEN). Subseqaently, the loaded column was washed by using 30 ml of a washing solution (20 mM imidazole, 50 mM Tris pH 8.0) containing 20 mM imidazole, and was eluted by using 5 ml of an eluent (400 mM imidazole, 50 mM Tris pH 8.0) containing 400 mM imidazole, in order to collect factions containing the liquid binding region of PPAR γ.

After a reaction solution (10 rm Tris pH 7.4, 50 mM KCl, 10 mM DTT) containing 10 μg of the collected ligand binding region of PPAR γ was prepared, BADGE (commercially available from Tokyokasei K.K.) and BRL49653 (commercially available from American Radiolabeled Chemicals Inc.) were added to the reaction solution, so that the final concentration of BADGE was 50 μM therein and the final concentration of the tritium labeled BRL49653 (commercially available from American Radiolabeled Chemicals Inc.) was 10 nM therein. Thereafter, the achieved reaction solution was allowed to sit at 4° C. for 3 hours. As a control, a solution, in which 1% DMSO instead of the BADGE was added to such a solution, was treated in a similar manner.

Subsequently, 0.1 ml of the achieved reaction solution was loaded onto a Quick Spin G-25 Sephadex column (commercially available from Boehringer Mannheim) to collect a fraction containing the tritium labeled BRL49653 which was bound to the ligand binding region of PPAR γ. The radio activity of the collected fraction was then measured on a liquid scintillation counter (hereinafter referred to as a "measured value") and a relative value of said fraction was then calculated, based on adjusting the measured value of the control as a value of 100. As a result, BADGE was found to suppress the binding of BRL49653 to the ligand binding region of PPAR γ at 53%.

Example 2

First, NIH3T3 cells (commercially available from Dainihon Seiyaku Co., Ltd.) were seeded into a 24 well plate (commercially available from Sumitomo Bakelite Co., Ltd.) in an amount of $5.0 \times 10^4$ cells per well and were cultured overnight. As such, the cells were cultured at 37° C., by using the D-MEM medium (high glucose content, commercially available from GIBCO) containing 10% fetal bovine serum (FBS), and in the presence of 5% carbon dioxide. Subsequently, 0.15 μg of a reporter plasmid ($UAS_{GX}4TK$-LUC), 0.10 μg of aplasmid (CMX-GAL-PPAR γ) for expressing a fused gene encoding a DNA binding region of yeast GAL4 and the ligand binding region of PPAR γ, and 0.25 μg of a plasmid (CMX-βgal) which expresses β-galactosidase as an internal standard were simultaneously added to each well, and such plasnids were introduced into the above cultured cells. The above plasmids were all obtained by according to a method described in Barry M. Forman, et al. (Cell 83, 803–812, 1995). In addition, the introduction of the above plasmids into the cells was carried out in accordance to a method using lipofectamine (commercially available from GIBCO). In other words, after a total 0.5 μg of the above plasmid DNAs and 1.75 μl of the lipofectamine reagent (commercially available from GIBCO) were suspended in 25 μl of Opti-MEM I medium (commercially available from GIBCO), respectively, both suspensions were mixed and allowed to sit at room temperature for 30 minutes. After 200 μl of Opti-MEM I medium was added to the mixed solution and was mildly mixed, the achieve mixed solution was added to cells which had been washed twice by use of Opti-MEM I medium, so that the cells can be cultured at 37° C. for 5 hours. Subsequently, after the cells, which were cultured in the wells, were washed once by use of a phosphate solution of PBS (commercially available from GIBCO), D-MEM medium (high glucose content, commercially available from GIBCO) containing 10% FBS (commercially available from GIBCO) was added thereto in an amount of 500 μl per well. BADGE (commercially available from Tokyokasei K.K.) or BRL49653, which was dissolved in DMSO, was then added to the achieved cells respectively, so that the BADGE and the BRL49653 each had a final concentration of 50 μM therein (wherein the final concentration of DMSO was 0.5%), and that was cultured overnight. The BRL49653 was prepared in accordance to a method described in Banrie C.C. Cantello, et al. (J. Med. Chem. 37,3977–3985, 1994). In addition, a control was also prepared by adding DMSO instead of BADGE or BRL49653 to a sample of prepared cells, so that the final concentration of DMSO was 0.5% therein.

The cells which were cultured in such a manner were then used to measure luciferase activity and β-galactosidase activity, respectively. The measurement of the luciferase activity was preformed by using a PicaGene luminescence kit (commercially available from TOYO INK MFG. CO., LTD.). In other words, after the cells which were cultured in said wells were washed once with PBS, the 5 fold concentrated cell lysis agent which was provided by the kit was diluted 5 fold by using water, and that was added to each of the wells in an amount of 50 μl per well. The wells were then allowed to sit at room temperature for 15 minutes. The achieved material in the wells was transferred to a centrifuge tube by using a pipette and that was centrifuged in order to recover the supernatant. Five microliters (5 μl) of the supernatant was added to 100 μl of a luminescence substrate solution and the luminescence amount of the achieved solution was measured for 30 seconds by use of a luminometer (commercially available from TURNER, TD-20e) hereinafter referred to as "measured value 1"). In addition, the measurement of the β-galactosidase activity was performed by adding 30 μl of the above supernatant to 470 μl of a reaction buffer [8.53 g/l of disodium hydrogenphosphate, 4.78 g/l of sodium dihydrogenphosphate, 0.75 g/l of potassium chloride, 0.246 g/l of magnesium sulfate heptahydrate, 2.7 ml/l of β-mercaptoethanol, and 1 g/l of O-NITOROPENYL β-D-GALACTOPYRANOSIDE (commercially available from Sigma)], thermostating which at a temperature at 37° C. for 3 to 4 hours, and measuring the absorbance of the achieved reaction solution at 420 nm (hereinafter referred to as "measured value 2"). The relative value of PPAR γ activation was then caulated by dividing the measured value 1 by the measured value 2, and by adjusting the achieved values, wherein said achieved values were based on adjusting the control to as 1. The results are given in Table 1.

As a result, it was found that BADGE does not allow PPAR γ to activate.

TABLE 1

| Test Compound | Relative values of PPAR γ activation |
|---|---|
| 50 μM BRL49653 | 83.0 |
| 50 μM BADGE | 1.0 |

Example 3

In a similar manner as that described in EXAMPLE 2, the plasmids of UAS$_{GX}$4TK-LUC, CMX-GAL-PPAR γ, and CMX-βgal were simultaneously introduced into NIH3T3 cells and the achieved cells were cultured for 5 hours. Then, after the cells which were in cultured in the wells were washed once with PBS, D-MEM medium (high glucose content, commercially available from GIBCO) containing 10% FBS (commercially avaiable from GIBCO) was added thereto in an amount of 500 μl per well. BADGE (conmmercially available from Tokyokasei K.K.) and BRL49653, which were dissolved in DMSO, were then added to the cells, so that BRL49653 had a final concentration of 0.1 μM therein and BADGE had a final concentration of 50 μM therein (wherein the final concentration of DMSO was 0.5%) and that was cultured overnight. Separately, a system in which BADGE was not added to a prepared culture of cells, but BRL49653 was added thereto, so that the final concentration of the BRL49653 0.1 μM therein (wherein, the final concentration of DMSO was 0.5%), and a system in which only DMSO was added to the cells, so that the final concentration of DMSO was 0.5% therein were also cultured similarly.

The cells which were prepared in such a manner were then used to measure luciferase activity and the β-galactosidase activity, respectively. The measurement of the luciferase activity was each carried out similarly to Experimental Example 2. In addition, the β-galactosidase activity was also carried out similarly to Experimental Example 2. The relative value of PPAR γ activation was then calculated by dividing the luminescence value of each according well by the absorbance value of each according well at the wavelength of 420 nm, and by additionally adjusting the achieved values, wherein said achieved values were based on adjusting the achieved value of the system which consisted of DMSO to as 1. The results are given in Table 2.

As a result, it was made clear that BADGE suppresses PPAR γ which is activated by BRL49653.

TABLE 2

| Test Compound | Relative value of PPARγ activation |
|---|---|
| 0.1 μM BRL49653 + 0.5% DMSO | 5.6 |
| 0.1 μM BRL49653 + 50 μM BADGE | 2.6 |

Example 4

(1) (a) Mouse 3T3-L1 cells (commercially available from Dainihon Seiyaku Co. Ltd) which were cultured in a medium that was prepared by adding Bovine Calf Serum (commercially available from Hyclone; hereinafter referred to as "BCS"), an aqueous penicillin solution (commercially available from Cellgro) and an aqueous streptomycin solution (commercially available from Cellgro) to Dulbecco's modified eagle medium (containing 4.5 g/l D-glucose and 584 mg/l L-glutamine; commercially available from Cellgro), so that the final concentration of the BCS was 10%, the penicillin was 100 units/ml, and the streptomycin was 100 μg/ml therein (hereinafter referred to as "BCS containing medium"), were suspended in additional BCS containing medium to amount to about $5 \times 10^4$ cells/ml. The achieved cell culture was deposited into 100×20 mm Falcon plates in an amount of 10 ml per well of the well plates, and said cells were cultured to confluence at 37° C. and in the presence of 5% $CO_2$. A solution of BADGE and ethanol was then added to the cells, so that the final concentration of BADGE was 100 μM therein, and that was cultured overnight.

(b) Separately, as a control, ethanol was only added to a culture of the confluent cells in a similar amount as that provided in the case which the solution of BADGE and ethanol was added thereto, and that was also cultured overnight.

(2) (a) The medium in each well was removed from the wells, and 2 ml of a medium which was prepared by adding Fetal Bovine Serum (commercially available from Hyclone) to amount to a concentration of 10% therein, penicillin (commercially available from Cellgro) to amount to a concentration of 100 units/ml therein, streptomycin (commercially available from Cellgro) to amount to a concentration of 10 μml there, insulin (conmmercially available from Sigma) to amount to a concentration of 5 μg/ml therein, dexamethasone (commercially available from Sigma) to amount to a concentration of 1 μM, and 3-isobutyl-1-methyl-xanthine (commercially available from Sigma) to amount to a concentration of 0.5 mM therein into Dulbecco's modified eagle medium (containing 4.5 g/l D-glucose and 584 mg/l L-glutamine; and commercially available from Cellgro), was then added to each well. In addition, a solution of BADGE and ethanol was then added to the cells, so that the final concentration of BADGE was 100 μM therein, and that was cultured for 2 days at 37° C. and in the presence of 5% $CO_2$.

(b) In addition, from the control cell culture achieved in (1)(b), and as similar to (2)(a), ethanol was only added to a culture of the confluent cells in a similar amount as that provided in the case which the solution of BADGE and ethanol was added thereto, and that was also cultured for 2 days at 37° C. and in the presence of 5% $CO_2$.

(3) (a) The medium in each well was removed from the wells, and 2 ml of a medium which was prepared by adding Fetal Bovine Serum (commercially available from Hyclone) to amount to a concentration of 10% therein, penicillin (commercially available from Cellgro) to amount to a concentration of 100 units/ml therein, streptomycin (commercially available from Cellgro) to amount to a concentration of 100 μg/ml therein, and insulin (commercially available from Sigma) to amount to a concentration of 5 μg/ml therein into Dulbecco's modified eagle medium (containing 4.5 g/l D-glucose and 584 mg/l L-glutamine; and commercially available from Cellgro), was then added to each well. In addition, a solution of BADGE and ethanol was then added to the cells, so that the final concentration of BADGE was 100 μM therein, and that was cultured for 2 days at 37° C. and in the presence of 5% $CO_2$.

(b) Furthermore, from the control cell culture achieved in (2)(b), and as similar to (3)(a), ethanol was only added to a culture of the confluent cells in a similar amount as that provided in the case which the solution of BADGE and ethanol was added thereto, and that was also cultured for 2 days at 37° C. and in the presence of 5% $CO_2$.

(4) (3)(a) and (3)(b) were repeated to each according culture of cells (i.e., a system containing BADGE and a system without BADGE)

(5) Each achieved cell culture was then treated with Oilred O (Sudan II; commercially available from Sigma) to stain the fat in the cells. As a result, the well containing the control cell culture (which does not contain BADGE) were stained by the Oilred O, but the well containing cell culture with 100 μM BADGE had the degree of staining suppressed.

From the invention this described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method of inhibiting the activation of PPAR γ in a mammal, which comprises administering an effective amount of bisphenol A diglycidyl ether to a mammal.

2. The method according to claim 1, wherein the mammal is a human.

3. The method according to claim 1, wherein the administration is oral.

4. The method according to claim 2, wherein the administration is oral.

5. The method according to claim 1, wherein the administration is parenteral.

6. The method according to claim 2, wherein the administration is parenteral.

7. A method for inhibiting the accumulation of fat in the adipose tissues in a mammalian body, which comprises administering an effective amount of bisphenol A diglycidyl ether to a mammal.

8. The method according to claim 7, wherein the mammal is a human.

9. The method according to claim 7, wherein the administration is oral.

10. The method according to claim 8, wherein the administration is oral.

11. The method according to claim 7, wherein the administration is parenteral.

12. The method according to claim 8, wherein the administration is parenteral.

13. A method for preventing or alleviating obesity of a mammal, which comprises administering an effective amount of bisphenol A diglycidyl ether to a mammal.

14. The method according to claim 13, wherein the mammal is human being.

15. The method according to claim 13, wherein the administration is oral.

16. The method according to claim 14, wherein the administration is oral.

17. The method according to claim 13, wherein the administration is parenteral.

18. The method according to claim 14, wherein the administration is parenteral.

* * * * *